United States Patent [19]
Gundersen

[11] 4,022,834
[45] May 10, 1977

[54] ANTIBACTERIALLY ACTIVE HEXAMETHYLENE-BIS-BIGUANIDES

[75] Inventor: Helge Guttorm Gundersen, Oslo, Norway

[73] Assignee: A/S Farmaceutisk Industri, Oslo, Norway

[22] Filed: May 1, 1975

[21] Appl. No.: 573,517

Related U.S. Application Data

[63] Continuation of Ser. No. 340,890, March 13, 1973, abandoned.

[30] Foreign Application Priority Data

Mar. 16, 1972 Norway .............................. 72864

[52] U.S. Cl. .................. 260/564 B; 260/343.7; 260/239 BA; 260/501.14; 424/280; 424/316; 424/326
[51] Int. Cl.$^2$ ..................................... C07C 129/16
[58] Field of Search ....... 260/564 B, 501.14, 343.7, 260/239 BA

[56] References Cited
UNITED STATES PATENTS 3,468,898   9/1969   Cutler et al. ................... 260/564 C

OTHER PUBLICATIONS

Rose et al., J. Chem. Soc. (London) 1956 pp. 4422–4425.

*Primary Examiner*—Gerald A. Schwartz
*Attorney, Agent, or Firm*—Wenderoth, Lind & Ponack

[57] ABSTRACT

There are disclosed new hexamethylene-bis-biguanides having antibacterial activity, and two processes for the preparation thereof. The new compounds have the general formula

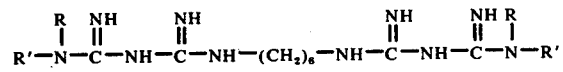

wherein R represents H, and R' represents an hexyl or pentyl group being substituted with one or two methyl groups, or represents a cycloalkyl group having more than 6 carbon atoms, a lower-alkyl-cycloalkyl group or a cycloalkyl-lower-alkyl group, or R and R' together with the adjacent nitrogen atom represent an azabicyclo(3,2,2)-nonane double ring.

5 Claims, No Drawings

ANTIBACTERIALLY ACTIVE HEXAMETHYLENE-BIS-BIGUANIDES

This is a continuation of application Ser. No. 340,890, filed Mar. 13, 1973, now abandoned.

This invention relates to new compounds having antibacterial activity.

According to the invention there are provided new hexamethylene-bis-biguanides of the general formula I:

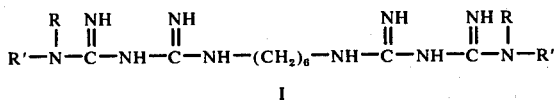

wherein R represents hydrogen and R' represents a hexyl or pentyl group substituted with one or two methyl groups, or represents a cycloalkyl group having more than 6 carbon atoms, a lower alkyl-cycloalkyl group or a cycloalkyl-lower-alkyl group, or R and R' together with the adjacent N-atom represents an azabicyclo-(3,2,2)-nonane double ring, and pharmaceutically acceptable acid salts thereof.

As used herein the term "cycloalkyl" comprises mono- as well as polycyclic alkyl groups. The term "lower alkyl" as used herein represents an alkyl group containing 1–4 carbon atoms.

According to another feature of the invention the new bis-biguanides are prepared in the following manners:

a. Hexamethylene-bis-dicyandiamide of the formula

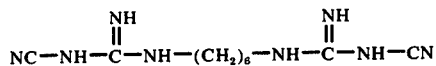

is reacted with an amine of the general formula RR'NH wherein R and R' have the above meaning. The reaction may be carried out by melting the reactants together at a temperature in the range 130°–180° C, or by using a suitable solvent.

b. 1,6-Diaminohexane of the formula

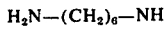

is reacted with a dicyandiamide of the general formula

wherein R and R' have the above meaning, under conditions corresponding to those indicated under item a).

In general the amine is used in the form of a salt with an inorganic acid in both alternatives a) and b), and hexamethylene-bix-biguanides will then be formed as the corresponding di-salt. The free base may be prepared in an ordinary manner, e.g. by reacting the salt with an equivalent amount of base, such as NaOH or $NH_3$.

The dicyandiamides employed as starting materials are prepared by known methods.

The pharmaceutically acceptable acid addition salts of the new hexamethylene-bis-biguanides comprise their salts with one or two equivalents of a suitable acid. A suitable acid addition salt is e.g. a salt with an inorganic acid, e.g. a hydrochloride, hydrofluoride, nitrate, sulfate or phosphate, or a salt with an organic acid, such as carboxylic acid, e.g. an acetate, benzoate, tartrate, adipate, lactate, maleate, glutamate, ascorbate, citrate, gluconate, oxalate, succinate, pamoate or salicylate. The salts are valuable e.g. due to the different solubility or the specific value of the anion. The salts may be prepared from the corresponding base or from salts with other acids by well known methods.

Hexamethylene-bis-biguanides are previously known. Thus, Norwegian Pat. No. 83.394 describes a number of compounds in which the terminal groups are substituted phenyl nuclei. One of these compounds, 1,1'-hexamethylene-bix-[5-(4-chlorophenyl)biguanide], has obtained an extensive use under trade name "chlorohexidine". The substance is primarily used because of its antibacterial effect, and it has been widely used for disinfection of skin and instruments of all types, hand wash, impregnation of wound dressings and storing of sterile utensiles. Odontologists have used the substance for disinfection of e.g. mucous membranes and root channels. It has also been used for treatment of skin infections, eye infections and in gynecological practice.

One of the newest fields of the use for chlorohexidine is for the prophylactic treatment against tooth and gum diseases. The substance inhibits the formation of the bacterial deposit called plaque, which is considered to be the predominant etiological factor both with respect to caries and gingivitis. Gingivitis occurs after 2–3 weeks if the plaque is allowed to accumulate on the tooth surface, while small decalcifications can be detected after about 4 weeks without oral hygiene. Rinsing of the mouth with chlorohexidine has been found to have a marked inhibiting effect on the formation of plaque and has therefore a prophylactic effect against gingivitis and caries.

In French Pat. No. 1.463.818 there is given a general formula comprising an extremely large number of compounds, i.a. some of the compounds of the invention. Of the specific compounds mentioned and described in the French patent, the one which is most closely related to the compounds prepared according to the invention is 1,1'-hexamethylene-bis-[5-(2-ethylhexyl)biguanide], with the generic name alexidine. This is a compound of the above general formula I in which R is hydrogen and R' is 2-ethylhexyl, and it is also known for having antibacterial activity.

The hexamethylene-bis-biguanides according to the invention, distinguish themselves from chlorohexidine and alexidine through at least one of the following properties: stronger antibacterial effect, stronger plaque-inhibiting effect or lower toxicity. The compounds are therefore valuable for such uses as e.g. the ones described above for chlorohexidine.

The advantages of the new hexamethylene-bis-biguanides are illustrated in the following:

PLAQUE-INDEX

Plaque-index on test persons after rinsing with 10 ml of 1,1 mM solution 3 times daily for 3 days. The rinsing was during this time the only type of oral hygiene used.

Plaque-index, which is a recognized measure of plaque-inhibiting property, runs from 0 (no plaque) to 3 (clearly visible plaque marginally).

| Compound No. | Compound of formula I R | R' | Plaque index |
|---|---|---|---|
| 1 | H | 1,5-dimethylhexyl | 0,36 |
| 2 | 3-azabicyclo(3,2,2)-non-3-yl | | 0,58 |
| 3 | H | cyclohexylmethyl | 0,19 |
| 4 | H | 1-adamantyl | 0,36 |
| 5 | H | 2-norbornyl | 0,50 |
| 6 | H | 1-methylhexyl | 0,27 |
| 7 | H | 1,3-dimethylpenthyl | 0,29 |

-continued

| Compound No. | Compound of formula I R | R' | Plaque index |
|---|---|---|---|
| 8 | H | 1,4-dimethylpenthyl | 0,70 |
| 9 (known) | H | 2-ethylhexyl | 0,52 |

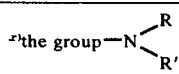

In comparison rinsing with 1,6 mM chlorohexidine under the same conditions gives a plaque-index of 0,75. This is considerably lower than traditional brushing with tooth paste.

ANTIBACTERIAL EFFECT

Inhibition of growth in aqueous solution and subcultivation in liquid medium. Reference: Chloro;hexidine=1.

| Compound | Staph. aureus | Aerobacter aerogenes |
|---|---|---|
| 1 | 4 | 16 |
| 2 | 1 | 1 |
| 3 | 2 | 8 |
| 4 | 16 | 8 |
| 5 | ½ | ⅛ |
| 6 | 4 | 1 |
| 7 | 8 | 1 |
| 8 | 8 | 1 |
| 9 (known) | 8 | 2 |

TOXICITY

Cytotoxic effect on human epithelial cells in vitro after treatment for 5 minutes at 37° C. Reference: Chlorohexidine=1.

| Compound | Cytotoxic effect relative to chlorohexidine |
|---|---|
| 2 | ⅛ |
| 3 | ½ |
| 5 | ⅛ |
| 6 | 1 |
| 7 | 1 |
| 8 | 1 |
| 9 (known) | 4 |

All the tested compounds according to the invention have thus a toxicity lower than or equal to that of chlorohexidine, while alexidine is much more toxic.

| ACUTE PERORAL TOXICITY IN MICE | |
|---|---|
| Compound | LD$_{50}$ |
| Chlorohexidine-digluconate | 1800 mg/kg |
| Compound 1-dichloride | 1690 mg/kg |
| Compound 4-dichloride | 2830 mg/kg |

The new compounds prepared according to the invention may be used for the same purpose mentioned above for chlorohexidine. Thus, their antibacterial activity may e.g. be utilised for disinfection, in dentifrices and mouth washes and for the treatment of infection in animals and humans.

EXAMPLE 1

7,7 g of 2-amino-6-methylheptane hydrochloride are mixed with 5,5 g hexamethylene-bis-dicyandiamide in a mortar. The mixture is allowed to react at 155° C for 5 hours, is cooled and extracted with boiling water. Upon cooling 1,1'-hexamethylene-bis-[5-(1,5-dimethylhexyl)biguanide]dihydrochloride crystallises. The product is recrystallized from methanol-ether.

| Melting point: | 225° C | | | |
|---|---|---|---|---|
| Calculated: | 53,69%C | 10,05%H | 24,08%N | 12,19%Cl |
| Found: | 52,17%C | 9,95%H | 24,23%N | 13,83%Cl |

EXAMPLE 2

14,5 g of 1,5-dimethylhexyl-dicyandiamide are mixed with 6,5 g of hexamethylene-diamine-dihydrochloride and reacted at 155° C for 5 hours. After working as in Example 1 a compound identical to the product described therein is obtained.

EXAMPLE 3

5,6 g of 1,4-dimethylpentyl-dicyandiamide and 2.7 g of hexamethylene-diamine-dihydrochloride are melted together and stirred at 155° C for 8 hours. The mixture is then dissolved in boiling water and treated with activated carbon. Upon cooling 1,1'-hexamethylene-bis-[5-(1,4-dimethylpentyl)biguanide]-dihydrochloride crystallises. Melting point: 223° C.

EXAMPLE 4

7,6 g of 1,3-dimethylpenthyl-dicyandiamide are reacted with 3,6 g of hexamethylene-diamine-hydrochloride for 8 hours at 155° C. Working as in example 3. There is obtained 1,1'-hexamethylene-bis-[5-(1,3-dimethylpenthyl)-biguanide]-dihydrochloride. Melting point: 212° C.

EXAMPLE 5

10,2 g of 1 -methylhexyl-dicyandiamide and 5,0 of hexamethylene-diamine-dihydrochloride are mixed and heated to 155° C for 7 hours and worked as in Example 3. Recrystallised from water/ethanol. There is obtained 1,1'-hexamethylene-bis-[5-(1-methylhexyl)-biguanide]-dihydrochloride. Melting point: 234° C.

EXAMPLE 6

4,5 g of (1-adamantyl)dicyandiamide and 1,8 g of hexamethylene-diamine-dihydrochloride are mixed with 10 ml of nitrobenzene and allowed to react at 160° C for 5 hours with stirring. After cooling the substance is filted off and recrystallized from ethanol. There is obtained 1,1'-hexamethylene-bis-[5-(1-adamantyl)-biguanide]dihydrochloride.

| Melting point: | 268° C. | | | |
|---|---|---|---|---|
| Calculated: | 57,58%C | 8,69%H | 22,50%N | 11,33%Cl |
| Found: | 56,97%C | 8,66%H | 22,26%N | 12,06%Cl |

EXAMPLE 7

3,5 g of 2-aminonorbornane-hydrochloride (norbornane=[2,2,1]-bicycloheptane) are mixed with 2,8 g of hexamethylene-bis-dicyandiamide and heated to 155° C for 2 hours. The substance is crystallized from water and recrystallized from methanol/ether. There is obtained 1,1'-hexamethylene-bis-[5-(2-endonorbornyl]-biguanide)-dihydrochloride.

| Melting point: | 225° C | | | |
|---|---|---|---|---|
| Calculated: | 52,87%C | 8,50%H | 25,67%N | 12,99%Cl |

| | | | | |
|---|---|---|---|---|
| Found: | 52,11%C | 8,59%H | 24,02%N | 13,01%Cl |

EXAMPLE 8

7,8 g of cyclohexane methylamine hydrochloride (hexahydrobenzylamine hydrochloride) and 6,2 g of hexamethylene-bis-dicyandiamide are mixed and heated to 155° C for 3 hours. The mixture is extracted with boiling water, decolorized with activated carbon, and crystallises upon cooling. The crude product is recrystallized from water. There is obtained 1,1'-hexamethylene-bis[5-cyclohexylmethyl)biguanide]-dihydrochloride.

| | | | | |
|---|---|---|---|---|
| Melting point: | 216° C. | | | |
| Calculated: | 52,44%C | 9,17%H | 25,49%N | 12,91%Cl |
| Found: | 52,41%C | 9,08%H | 25,46%N | 12,89%Cl |

EXAMPLE 9

7,8 g of 3-azabicyclo(3,2,2)nonane-hydrochloride and 5,8 g of hexamethylene-bis-dicyandiamide are allowed to react at 150° C for 2½ hours. The reaction mixture is worked as in Example 8, and the crude product is recrystallized from methanol/ether. There is obtained a compound of formula I in which

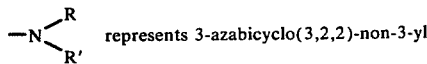

| | | | | |
|---|---|---|---|---|
| Melting point: | 216° C. | | | |
| Calculated: | 54,43%C | 8,79%H | 24,42%N | 12,36%Cl |
| Found: | 52,92%C | 8.88%H | 24,10%N | 11,78%Cl |

The identities of all the compounds prepared have been confirmed by IR-spectra.

What is claimed is:

1. A compound of the formula

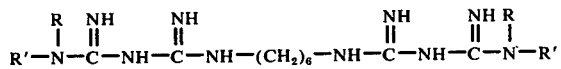

wherein R represents H and R' is selected from the group consisting of 1-adamantyl, 2-norbonyl and cyclohexylmethyl or wherein R and R' together with the adjacent nitrogen atom form a 3-azabicyclo(3,2,2)-nonane double ring and pharmaceutically acceptable acid addition salts.

2. Compound according to claim 1, wherein R'=1-adamantyl and R=H.

3. Compound according to claim 1, wherein R'=2-norbornyl and R=H.

4. Compound according to claim 1, wherein R'=cyclohexylmethyl and R=H.

5. Compound according to claim 1, in which R' and R together with the adjacent nitrogen atom form a 3-azabicyclo(3,2,2)-nonane double ring.

* * * * *